United States Patent [19]
Augst et al.

[11] Patent Number: 5,616,387
[45] Date of Patent: Apr. 1, 1997

[54] PERFORATED ROLL OF ELASTIC WRAP

[75] Inventors: George W. Augst, Forest Lake; Margo A. Liberda, Stillwater; John E. Riedel, Hugo, both of Minn.

[73] Assignee: Minnesota Mining and Manufacturing Company, St. Paul, Minn.

[21] Appl. No.: 543,511

[22] Filed: Oct. 16, 1995

Related U.S. Application Data

[63] Continuation-in-part of Ser. No. 259,613, Jun. 14, 1995, abandoned, which is a continuation-in-part of Ser. No. 114,912, Aug. 31, 1993, abandoned.

[51] Int. Cl.⁶ .................................................... C09J 7/02
[52] U.S. Cl. ............................ 428/43; 428/343; 428/352; 428/354; 428/906
[58] Field of Search ............................ 428/43, 261, 343, 428/352, 354, 906, 230, 231

[56] References Cited

U.S. PATENT DOCUMENTS

| | | |
|---|---|---|
| Re. 24,906 | 12/1960 | Ulrich . |
| 2,308,693 | 1/1943 | Goldman . |
| 2,508,855 | 5/1950 | Brown . |
| 2,532,011 | 11/1950 | Dahlquist et al. . |
| 2,870,840 | 1/1959 | Kwitek . |
| 3,085,024 | 4/1963 | Blackford . |
| 3,121,021 | 2/1964 | Copeland . |
| 3,143,208 | 8/1964 | Sizemore . |
| 3,173,826 | 3/1965 | Campbell et al. . |

(List continued on next page.)

FOREIGN PATENT DOCUMENTS

| | | |
|---|---|---|
| 886474 | 1/1962 | United Kingdom . |
| WO93/15245 | 8/1993 | WIPO . |

OTHER PUBLICATIONS

Product Brochure entitled: "Elastoplast™ Latex" (2 pages), before Aug., 1993.
Instructions for the Model #211-300 Handle-O-Meter (12 pages), before Aug., 1993.

*Primary Examiner*—Jenna Davis
*Attorney, Agent, or Firm*—Gary L. Griswold; Walter N. Kirn; Robert W. Sprague

[57] ABSTRACT

A roll of perforated, elastic wrap including a plurality of longitudinally spaced, laterally extending, perforated separation lines defined by a series of about 0.2 to 5 mm perforations separated by about 0.1 to 1 mm connecting segments of dressing where the ratio of perforation length to connecting segment length in each separation line is about 1:1 to 10:1 wherein the wrap can be longitudinally elongated between about 7 to 280 percent.

23 Claims, 2 Drawing Sheets

U.S. PATENT DOCUMENTS

| | | | |
|---|---|---|---|
| 3,331,728 | 7/1967 | Lane . | |
| 3,485,706 | 12/1969 | Evans . | |
| 3,486,186 | 12/1969 | Richards et al. . | |
| 3,493,462 | 2/1970 | Bunting, Jr. et al. . | |
| 3,494,821 | 2/1970 | Evans . | |
| 3,508,308 | 4/1970 | Bunting, Jr. et al. . | |
| 3,575,782 | 4/1971 | Hansen . | |
| 4,017,002 | 4/1977 | Doyle et al. | 221/63 |
| 4,292,360 | 9/1981 | Riedel et al. | 428/171 |
| 4,294,240 | 10/1981 | Thill . | |
| 4,298,647 | 11/1981 | Cancio et al. | 428/167 |
| 4,346,700 | 8/1982 | Dunshee et al. . | |
| 4,366,814 | 1/1983 | Riedel | 128/156 |
| 4,380,564 | 4/1983 | Cancio et al. | 428/167 |
| 4,465,729 | 8/1984 | Cancio et al. | 428/167 |
| 4,562,102 | 12/1985 | Rabuse et al. | 428/43 |
| 4,581,087 | 4/1986 | Johnson . | |
| 4,601,937 | 7/1986 | Latuseck | 428/132 |
| 4,606,338 | 8/1986 | Greenway et al. | 128/156 |
| 4,671,266 | 6/1987 | Lengyel et al. | 128/156 |
| 4,704,113 | 11/1987 | Schoots | 604/379 |
| 4,728,571 | 3/1988 | Clemens et al. | 428/352 |
| 4,737,393 | 4/1988 | Linkous | 428/43 |
| 4,768,810 | 9/1988 | Mertens | 282/12 A |
| 4,772,499 | 9/1988 | Greenway | 428/43 |
| 4,882,213 | 11/1989 | Goddis et al. | 428/136 |
| 4,908,251 | 3/1990 | Iimura et al. | 428/68 |
| 4,947,567 | 8/1990 | Hermann | 40/299 |
| 4,957,795 | 9/1990 | Riedel | 428/74 |
| 4,967,740 | 11/1990 | Riedel | 128/156 |
| 4,973,513 | 11/1990 | Riedel | 428/252 |
| 4,984,584 | 1/1991 | Hansen et al. | 128/898 |
| 5,016,331 | 5/1991 | Dilo | 28/115 |
| 5,088,483 | 2/1992 | Heinecke | 602/46 |
| 5,114,771 | 5/1992 | Ogg et al. | 428/43 |
| 5,160,315 | 11/1992 | Heinecke et al. | 602/57 |
| 5,198,276 | 3/1993 | Nakajima | 428/43 |
| 5,202,190 | 4/1993 | Kantner et al. | 428/447 |
| 5,213,565 | 5/1993 | Rollband | 602/41 |
| 5,230,701 | 7/1993 | Meyer et al. | 602/76 |
| 5,496,605 | 3/1996 | Augst . | |

5,616,387

PERFORATED ROLL OF ELASTIC WRAP

FIELD OF THE INVENTION

This is a Continuation of Ser. No. 08/259,613 filed Jun. 14, 1995 now abandoned which is a continuation in part of Ser. No. 08/114,912, filed Aug. 31, 1993 now abandoned. The invention relates to elastic wraps. More specifically, the invention relates to rolls of elastic wraps.

BACKGROUND

Elastic wraps are primarily used to wrap injuries. When correctly placed, elastic wraps impart support to strained tendons ligaments or muscles and/or apply continuous pressure to lacerations to reduce bleeding. Some of the most effective wraps exhibit both stretch and elasticity. Stretch is important to ensure that movement of a wrapped limb or joint is not unduly restricted by a wrap and also to ensure that blood flow to the affected area is not restricted. Elasticity ensures that the wraps return to their initial shape after being stretched by the patient in order to provide continuing support to the wrapped injury.

Elastic wraps are increasingly used in industries where injuries are quite prevalent. Examples of such industries include the meat packing industry and professional athletics. The private sector also uses elastic wraps for injuries incurred during recreational activities. When the wraps are used in the private sector or in industry, the injured individual commonly will apply the wrap to the injury without assistance from another person. Ideally, dispensing elastic wraps would not require assistance from another person.

Elastic wraps are commonly sold in strips in roll form. Rolling condenses the strips and also eases dispensing of the wrap without risk of tangling the wrap. In order to dispense elastic wrap, the desired length of elastic wrap is unrolled by unwinding the desired length. The wrap is then cut with a pair of scissors or similar cutting instrument. This method of dispensing is quite cumbersome and very difficult if an injured person must dress her own injury.

Ideally, a cutting instrument would not be required to sever the wraps at the appropriate length. However, due to the construction of elastic wraps, a cutting instrument such as a scissors is usually required to cut the wrap.

Elastomeric wraps are known in the art and are described in U.S. Pat. Nos. 5,230,701, 3,575,782, 4,366,814, and 4,984,584, the disclosure of which are hereby incorporated by reference. The wraps are formed of varied materials including but not limited to nonwoven fabrics, films and foams.

Many wraps are comprised of unoriented nonwoven fabrics. The random orientation of fibers of these fabrics provides useful properties and characteristics. One of these characteristics is the ability of such fabrics to resist continued linear tearing in the cross direction after introduction of an initial tear in the fabric. While this resistance-to-split characteristic of nonwoven fabrics is a beneficial attribute for various applications, it presents certain difficulties when nonwoven fabrics are used for wraps dispensed from a roll because a cutting instrument such as a scissors is necessary to dispense the fabric. Beyond the properties of the fabrics used to manufacture wraps, the fact that the wraps are elastic make the wraps exceedingly difficult to tear. When one attempts to tear an elastic wrap, the elastic wrap is stretched rather than torn due to the resiliency of the wrap. If one does succeed in tearing an elastic wrap, the resulting tear is usually uneven. Due to the difficulty in tearing elastic wraps and the resulting nonlinear tears if the wrap is torn, a tearable elastic wrap is needed.

One approach to providing a tearable nonwoven web is disclosed in Greenway, U.S. Pat. No. 4,772,499. Greenway suggests applying binder to the nonwoven web in spaced linear bands so that the web can be torn in a linear fashion along the binder-free bands of web. Unfortunately, the cost of producing such a banded nonwoven web is prohibitive for many purposes and differences in the surface characteristics of the web as between the binder-free and binder-containing bands would significantly complicate manufacture of the web. It is also perceived that such bands would detract from the performance of the tape.

Patent Cooperation Treaty Publication WO 93/15245 filed by the Minnesota Mining and Manufacturing Company of St. Paul, Minn. discloses an embossed nonwoven tape including both staple and binder fibers. The specific composition of the tape in combination with the embossed pattern on the tape renders the tape tearable in the cross-machine direction along an embossed pattern in the tape. The tearable tapes disclosed by this publication are limited to those which include a significant proportion of melt-activated binder fibers.

A need exists for elastic wraps in roll form which can be dispensed without the need for scissors or other cutting tools and which tear cleanly and evenly.

SUMMARY OF THE INVENTION

According to the present invention, elastic wraps are provided which are capable of being dispensed without the need for cutting tools. The roll of elastic wrap includes a plurality of longitudinally spaced, laterally extending, perforated separation lines defined by a series of about 0.2 to 5 mm perforations separated by about 0.1 to 1 mm connecting segments of wrap where the ratio of perforation length to connecting segment length in each separation line is about 1:1 to 10:1. The perforations allow the wrap to be torn along the perforation line. However, the perforations do not unduly weaken the stretch and/or the elasticity of the wrap. The invention therefore provides an elastic wrap which is tearable yet functional enough to provide support to injuries.

DETAILED DESCRIPTION OF THE INVENTION

The elastic wrap 10 of the present invention is comprised of a nonwoven web, a film, a foam or a woven fabric which exhibits stretch and recovery in one or more directions. For the purposes of this disclosure the term elastic is defined as having the property of generally returning to an original size or shape after stretching. One skilled in the art will recognize that the property of elasticity is a continuum. Some surgical tapes are mostly nonelastic while other tapes and wraps may exhibit a large degree of elasticity. The elastic property as characterized by the materials of the invention is defined as having a recovery, after stretching, wherein the material returns to at least 90% of its original shape within a two minute time period with a recovery force of at least 50% of the force required to stretch the material.

As stated above, elastic nonwoven fabrics are among the materials suitable for constructing the wraps of the invention. Elastic nonwoven fabrics are best known as constructed of 1) a composite of an elastic web and a nonwoven fabric, 2) a resin bonded to a web of elastic nonwoven fabric, or 3) stretchable nonwoven fabric bonded by an elastomer. The present invention anticipates that other constructions of elastic materials comprised of nonwoven webs will also be suitable for practicing the present invention. U.S. Pat. Nos. 5,230,701, 4,984,584, 4,366,814 and 3,575,782 all disclose elastic materials comprised of nonwoven webs which are each herein incorporated by reference.

Other fabrics, films and foams are also suitable for constructing the wraps of the invention. For example, elastic films such as polyurethene films are readily available and are suitable for the invention. Likewise, elastic foams such as polyvinylchloride, polyethylene and polyurethane foams are also suited for the invention.

The invention is described both by its appearance and also by its composition. To describe the appearance of the wrap of the invention, we turn to FIGS. 1 through 4.

Figure 1:
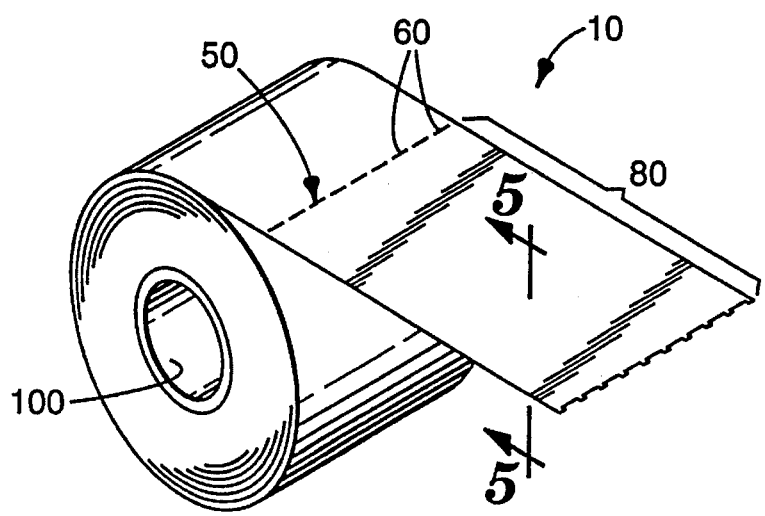
FIG. 1 is a perspective view of one embodiment of a roll of elastic wrap manufactured in accordance with the present invention.
Figure 2:
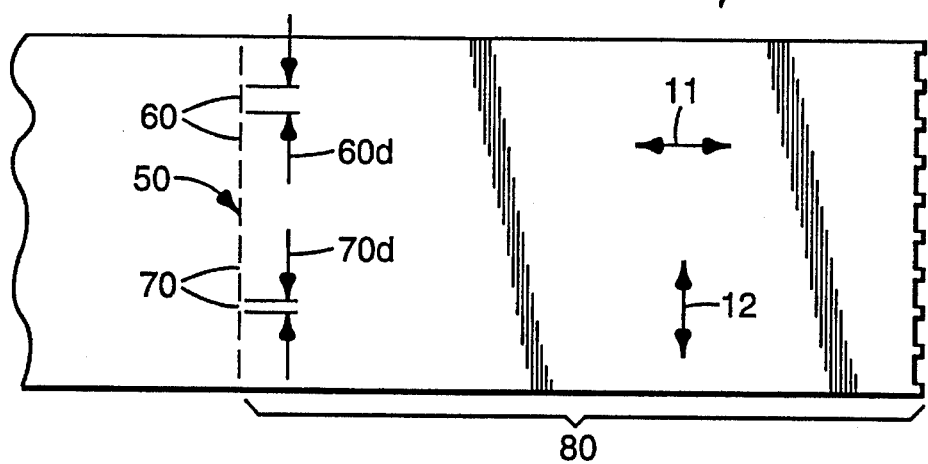
FIG. 2 is a top view of the elastic wrap of FIG. 1.
Figure 3:
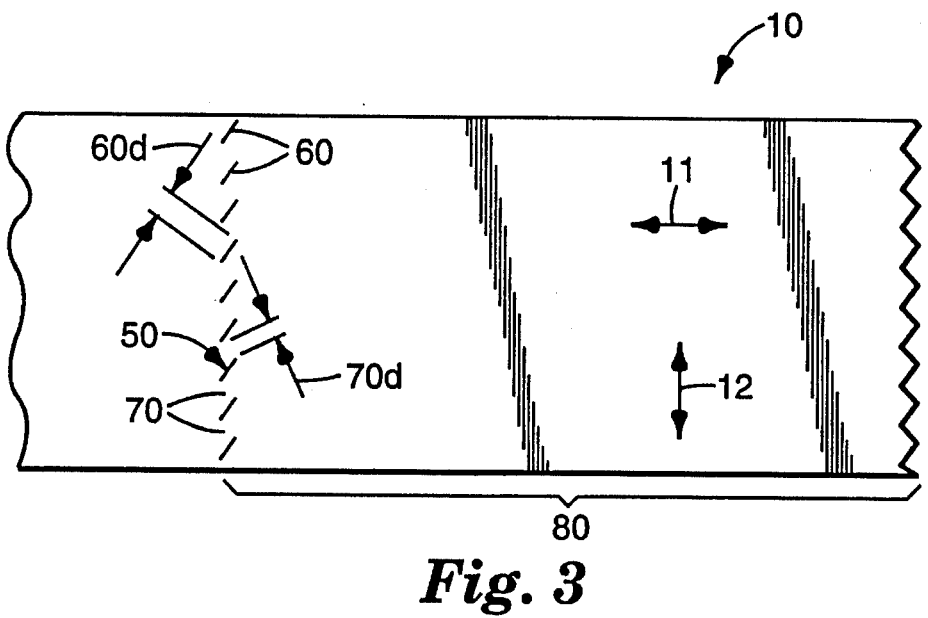
FIG. 3 is a top view of a first alternative embodiment for the separation line in the elastic wrap of the present invention.
Figure 4:
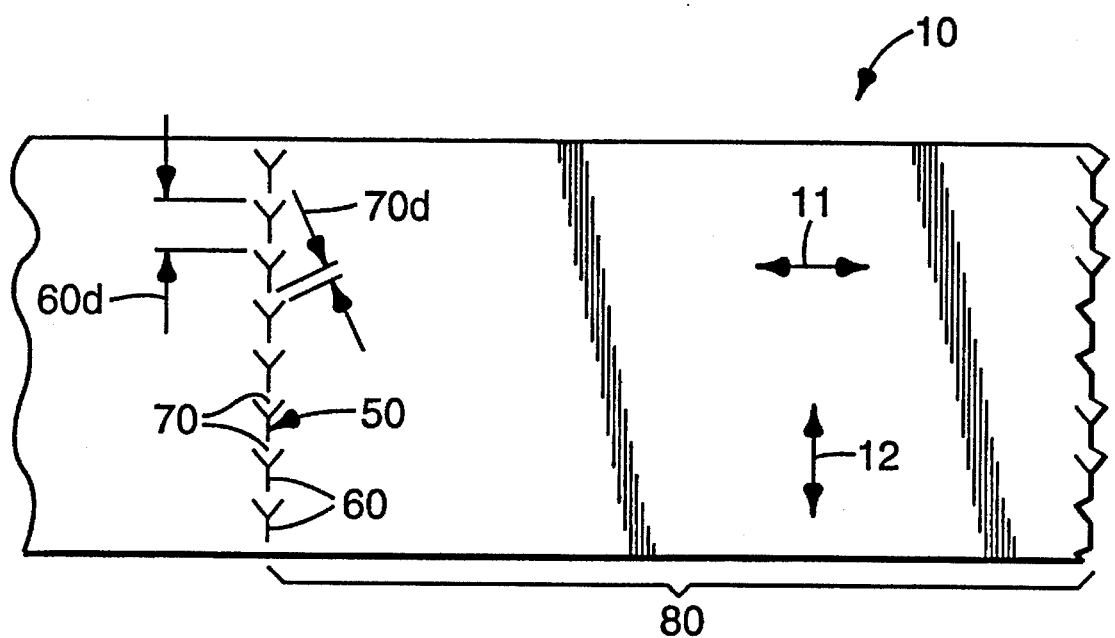
FIG. 4 is a top view of a second alternative embodiment for the separation line in the wrap of the present invention.

In a preferred embodiment, the elastic wrap 10 is rolled onto core 100 (FIG. 1). Elastic wrap 10 has a longitudinal direction 11 or machine direction and a lateral direction 12 or cross machine direction. To facilitate dispensing individual sheets of elastic wrap 80 from the roll, perforated separation lines 50 extending laterally across the elastic wrap are uniformly spaced longitudinally along the length of the roll. As seen in FIGS. 2 and 3, each separation line 50 is defined by a series of perforations 60, each of which has a perforation length 60D between about 0.2 and 5 mm. The connecting segments 70 between the perforations 60 are between about 0.1 and 1 mm in length (70D). The ratio of the perforation length 60D to the connecting segment length 70D is about 1:1 to 10:1. For the purposes of this disclosure a "roll" is defined as wraps wound on a core, wound about itself without a core, or loosely folded.

Perforation length 60D is measured as the distance between the longitudinal lines passing through the lateral extremities of the two connecting segments bonding the perforation 60. Connecting segment length 70D is the shortest distance between adjacent perforations 60.

Elastic wraps benefit by incorporating the separation lines 50 described herein. One would expect elastic wraps incorporating the separation lines of the invention to fail, either by prematurely tearing during dispensing or during application or by limiting the elasticity of the wrap. However, when prepared according to the present invention, the perforated elastic wraps do not fail but instead remain elastic and stretchable. The perforations also allow the user to tear the wrap in a linear fashion.

Composition

Nonwoven Webs

Where the wrap of the present invention consists of a nonwoven web, the web may be manufactured by any of the well known methods for manufacturing nonwovens including but not limited to melt-blowing, chemically-blowing, spin-bonding, carding, and hydrodynamic entanglement. A particularly preferred method for making a nonwoven web useful in the practice of this invention is by a technique known as hydroentangling. This process is described in U.S. Pat. Nos. 3,485,706, 3,486,168, 3,493,462, 3,494,821 and 3,508,308 incorporated herein by reference. Briefly, fibers are supported on a perforated plate or similar support screen and traversed with high energy liquid streams so as to consolidate the material in a repeating pattern of entangled fiber regions and interconnecting fibers. An alternate method of forming a nonwoven web is needle-tracking as described in U.S. Pat. No. 5,016,331 also incorporated herein by reference.

In order to make nonwoven webs elastic, elastic filaments must be bound to the web. This process is more fully described below. Other methods of elasticizing which are commonly known in the art may alternatively be used to make the web elastic.

When manufacturing elastic wraps of nonwoven webs, the thickness of the nonwoven web is about 0.1 to about 0.4 mm. The weight of the nonwoven web is preferably about 10 $g/m^2$ to about 120 $g/m^2$. The fabric composition and weight selection of the nonwoven web is determined by the product construction and the desired properties of the finished product. Webs used in laminated fabrics bonded together with elastomers or thermally bonded to stretched elastomeric filaments or other webs are usually light weight, about 10–25 $g/m^2$. Single layer fabrics bonded with elastomeric binders or elastomeric fiber fabrics are typically medium weight fabrics in the range of about 30–90 $g/m^2$ basis weight.

Preferred nonwoven webs include a family of high-strength nonwoven fabrics available from E. I. Dupont de Nemuours & Company of Wilmington, Del. under the trademark SONTARA™ including SONTARA™ 8010, a hydroentangled polyester fabric. Other suitable nonwoven webs include a hydroentangled polyester fabric available from Veratec, a division of International Paper of Walpole, Mass. This fabric is preferably bonded with HYSTRETCH™ V-43 binder, an elastomeric terpolymer available from the B F Goodrich Company. Another suitable nonwoven web is the nonwoven elastomeric web described in U.S. Pat. No. 5,230,701, which is herein incorporated by reference.

Binders

In one embodiment of the invention, the nonwoven web may include one of the well known binders for enhancing bonding of the individual fibers within the web. Selection of a suitable binder (i.e., one which has a suitable affinity for the fibers of the nonwoven web) is well within the judgment of one skilled in the art. Briefly, binders for nonwoven fabrics are typically selected from such materials as homopolymer and copolymer latexes of acrylics, butadienes, styrene/butadiene rubber copolymers, urethanes, vinyl acetates, vinyl acetate/acrylate copolymers, vinyl acetate/ethylene copolymers, polyvinyl alcohols, polyvinyl chlorides, vinyl esters, vinyl ethers, etc.

Specific examples of latex binding agents include, RHOPLEX™ E-2559 (an approximately 45% solids acrylic latex binder) available from the Rohm & Haas Co. of Philadelphia, Pa.; UNICAL™ 76-4402 (an approximately 50% solids styrene/butadiene rubber latex) available from the UNICAL Corp. of Charlotte, N.C.; NATIONAL STARCH™ No. 78-6283 (an approximately 45% solids acrylic/vinyl acetate copolymer latex) available from the National Starch Corp. of Bridgewater, N.J.; and the KRATON™ family of thermoplastic rubbers available from the Shell Oil Company of Oak Brook, Ill.

Additional binders include the various thermoplastic fibers which may be incorporated directly in the nonwoven web. The nonwoven web is bonded by simply incorporating about 5 to about 10 wt % of a compatible thermoplastic fiber into the nonwoven web and heating the web above the softening temperature of the thermoplastic fibers so as to bond the thermoplastic fibers to the staple fibers in the web. A compatible thermoplastic fiber is a fiber capable of melt-bonding to the other fibers in the web without substantially weakening the web.

Binder fibers are available in a wide variety of configurations including totally meltable binder fibers, side-by-side binder fibers, bicomponent binder fibers, elliptical core-sheath binder fibers, concentric core-sheath binder fibers, and combinations thereof.

Examples of suitable binder fibers include, binder fibers of polyester, polyethylene, polypropylene, polybutylene, polyamide and combinations thereof. The binder fibers are preferably from about 1 cm to about 20 cm in length and display a fineness of from about 0.1 denier to about 20 denier.

Specific examples of suitable core-sheath binder fibers for use in the nonwoven web include, DIAWA™ binder fibers (1½ denier by 38 mm crystalline polypropylene core with meltable polyethylene sheath) and MELTY™ binder fibers (2 denier by 38 mm oriented polyester core with meltable polyester sheath) available from Chori America, Inc. of Los Angeles, Calif.; and K-52™ binder fibers (2 denier by 38 mm oriented polyester core with meltable polyester sheath) and K-54™ binder fibers (2 denier by 38 mm oriented polyester core with meltable polyester sheath) available from Hoechst Celanese Corp. of Charlotte, N.C.

The enhanced fiber bonding achieved with binders tends to stiffen the web and thereby facilitate tearing of the web, improve handleability of the wrap 10 during application, and control fraying of the fibers along the tear line. However, as understood by those skilled in the art, when intended for use as elastic wrap 10, the amount of binder employed must be controlled so as to provide the wrap 10 with a softness and conformability acceptable to both health care professionals and patients. The surgical wrap 10 should possess sufficient stiffness to facilitate application of the wrap 10 while retaining sufficient conformability to be comfortable to the patient and maintain contact with the skin over prolonged periods of use:

Elastic Filaments

Elastic filaments are bound to the nonwoven web with an elastomeric binder such as concentrated natural rubber latex to obtain a highly elastic wrap. A wrap which is bonded with concentrated natural rubber coherently bonds to itself. Alternatively, wraps may be bound with polymers such as styrenebutadiene copolymers, such wraps do not coherently bond to themselves.

Films and Foams

A description of elastic films suitable for use with the present invention can be found in U.S. Pat. Nos. 5,088,483 and 5,160,315 the disclosures of which are hereby incorporated by reference. Particularly preferred films are elastomeric polyurethane, polyester, or polyether block amide films.

Foams such as polyvinylchloride, polyethylene and polyurethane foams are suitable foams for use with the present invention.

Adhesive

If an adhesive is employed, the adhesive is a pressure sensitive adhesive which, in the case of elastic wraps, is physically and biologically compatible with human skin. A wide variety of suitable, skin-compatible, pressure sensitive adhesives are known to those skilled in the art and include specifically, but not exclusively, acrylic-based adhesives, polyolefin adhesives, rubber-based adhesives, tackified styrene block copolymer adhesives, and the like.

A preferred pressure sensitive adhesive is any of the acrylate copolymers such as copolymers of isooctyl acrylate and acrylic acid or acrylamide described in U.S. Pat. No. Re. 24,906 issued to Ulrich which is incorporated herein by reference. Such adhesives are preferred for use on elastic wraps since they are relatively nonirritating to the skin.

The adhesive is optionally coated on a major surface of the elastic wrap. The wrap shown in FIG. 1 includes a top surface 32 and an opposing bottom surface 42. The adhesive may be coated on the top surface 32, the bottom surface 42, or on both surfaces.

Low Adhesion Backsize

If an adhesive is employed, a layer of low adhesion backsize is preferably applied to the opposite side of the substrate. For example, if adhesive is coated on surface 42, shown in FIG. 1, the low adhesion backsize would preferably be applied to opposing surface 32 of the elastic wrap. Application of low adhesion backsize to the elastic wrap provides a surface with a reduced adhesive affinity for the pressure sensitive adhesive. Such reduced adhesion facilitates the unwinding of wrap from a linerless roll of the wrap.

Materials suitable for use as a low adhesion backsize in this invention, include acrylates, fluorochemicals, polyethylenes, silicones, vinyl copolymers and combinations of these compounds. Compounds suitable as a low adhesion backsize are disclosed in U.S. Pat. No. 4,728,571 issued to Clemens et al, which is herein incorporated by reference. A specific example of a suitable low adhesion backsize is SYL-OFF™, a silicone compound available from Dow Corning Corp. Preferred low adhesion backsize are the siloxane and acrylate based compounds disclosed in U.S. Pat. No. 4,973,513 issued to Riedel and the water-insoluble hydrophobic urethane (carbamate) copolymer of polyvinyl alcohol and octadecyl isocyanate disclosed in U.S. Pat. No. 2,532,011 issued to Dahlquist et al both of which are herein incorporated by reference.

Separation Lines

The relative lengths 60*d* and 70*d* of perforations 60 and connecting segments 70 control several fundamental properties of wrap 10 related to dispensibility and performance. For example, length 70*d* of the connecting segments 70 is one factor controlling the tensile strength between individual sheets 80 of wrap 10. Separation of sheets 80 becomes difficult when the connecting segments 70 are too long while accidental and unintended separation is more likely when the connecting segments 70 are too short.

The physical dimensions of the perforations 60 and connecting segments 70 defining the separation lines 50 are important aspects of the invention. An acceptable balance must be achieved between the competing interests of adequate tensile strength to prevent premature separation and sufficient reduction in tensile strength to ensure easy and consistent separation of sheets 80 along a single separation line 50.

The parameters of separation lines 50 necessary to define performance are perforation length 60d, connecting segment length 70d and the ratio of perforation length 60d to connecting segment length 70d. Acceptable values for achieving proper performance of the perforated wrap 10 of this invention are set forth below in Table One. The interdependence of these variables and the cooperational manner in which they effect and influence performance of the wrap 10 requires that they be considered together.

The tensile strength of the perforated section of wrap 10 in the longitudinal direction 11 (FIG. 2) measured in accordance with the protocol set forth herein, is desirably from about 400 to about 3000 grams/cm width, preferably from about 600 to about 2000 grams/cm width, and most preferably from about 800 to about 1700 grams/cm width. A longitudinal tensile of less than about 400 grams/cm width tends to result in premature separation of the sheets 80 while a longitudinal tensile of greater than about 3000 grams/cm width tends to require excessive force and thereby hinder separation of the sheets 80.

TABLE ONE

| Variable | Acceptable | Preferred | Highest Performance |
| --- | --- | --- | --- |
| Perforation Length (mm) | 0.2–5.0 | 0.5–3.0 | 1.0–2.0 |
| Connecting Segment Length (mm) | 0.1–1.0 | 0.2–0.8 | 0.3–0.6 |
| Ratio Perforation Length -to- Connecting Segment Length | 1:1 to 10:1 | 1:1 to 6:1 | 1:1 to 3:1 |

A secondary consideration is the shape of the perforations 60 and connecting segments 70. Shape is designated as a secondary consideration because, while relevant to dispensibility and performance of the wrap 10, its impact is not as critical as the primary considerations of perforation length 60d, connecting segment length 70d and ratio of perforation length 60d to connecting segment length 70d. The perforations 60 may be shaped in accordance with any of the accepted perforation patterns including linear, angled, Y-shaped, V-shaped, dual-angled offset, sinusoidal, etc. When angled, the perforations 60 are preferably angled about 30° to 60° from the lateral axis 12 of the wrap 10. The preferred shape, based upon ease of manufacture and minimization of fraying along the torn edge, is a simple linear pattern extending laterally across the wrap 10 as shown in FIG. 2.

Similarly, the longitudinal distance 70d between the separation lines 50 must be selected so as to balance the competing interests of permitting substantially any length of wrap 10 to be created (more separation lines 50) and limiting the accidental and unintended separation of the wrap 10 along a separation line 50 during dispensing, application or use (fewer separation lines 50). Generally, a longitudinal spacing of about 1 to about 20 cm, preferably about 2 to about 10 cm provides an acceptable balance between these competing interests.

Method of Manufacture

Nonwoven Web Construction

Application of Binder

A binder may optionally be applied after formation of a nonwoven web by any of the conventional water or solvent-based coating techniques including air knife, trailing blade, direct and offset gravure, Meyer bar, wire-wound rod, reverse roll, roll coating, print bond and spray coating. Where the binder is a thermoplastic fiber, the fiber is simply dispersed into the fiber matrix prior to formation of the web and then melted.

Application of Elastic Filaments

For wraps having a high degree of elasticity, elastic yarns or filaments such as Lycra™ Spandex or linear polyurethane monofilament are bound to the nonwoven web with a fluid binder. A suitable binder is natural rubber latex at 60% concentration as disclosed in U.S. Pat. No. 3,575,782 which is herein incorporated by reference. The elastic filaments are stretched before and during binding and drying. Relaxing the bound elastic filament/rubber/nonwoven web composite causes shirring of the nonwoven web and results in an elastic wrap.

Application of Low Adhesion Backsize

Similarly, the low adhesion backsize may be applied by any of the conventional coating techniques discussed in connection with the application of a binder.

A dried coating weight of about 0.1 to about 0.4 mg/cm$^2$ is preferred for the low adhesion backsize and about 0.2 to 0.8 mg/cm$^2$ for the binder.

The binder and the low adhesion backsize may optionally be mixed together and simultaneously coated onto the nonwoven web in accordance with the procedure outlined in the Examples section of this disclosure and disclosed in U.S. Pat. No. 4,967,740 issued to Riedel and assigned to Minnesota Mining & Manufacturing Company of St. Paul, Minn. herein incorporated by reference.

Application of Adhesive

The pressure sensitive adhesive may be applied to the substrate by any of the well known techniques for coating pressure sensitive adhesives such as dispersion coating, solution coating and hot melt application. A convenient method of coating the substrate with the pressure sensitive adhesive is disclosed in U.S. Pat. No. 3,121,021 issued to Copeland herein incorporated by reference. Briefly, a pressure sensitive adhesive is coated on a smooth release liner. The release liner carrying the adhesive film is then laminated to the substrate, the release liner peeled away, and the linerless wrap 10 wound into a "jumbo" roll.

Alternatively, the adhesive may be applied by such conventional coating techniques as air knife, trailing blade, direct and offset gravure, wire-wound rod, reverse roll, print bond, spray coating, etc.

Perforating

The separation lines 50 are conveniently created with a rotary die having a serrated perforator blade(s) positioned along the periphery of the die so as to perforate the wrap 10 at the desired intervals. Other perforation methods known in the art, e.g., laser perforation, may also be used.

Converting

The "jumbo" rolls of wrap 10 are converted into multiple rolls of commercially sized wrap 10 by conventional converting techniques including unwinding, longitudinal slitting, rewinding, and lateral cutting.

Method of Use

The wrap 10 is dispensed by simply gripping the free end of the wrap, unrolling the desired length, and then tearing the wrap along a separation line 50. When separating the desired length of wrap from the roll, it is generally desired to grip the sheet 80 of wrap 10 closest to the roll to prevent other separation lines 50 from tearing.

Utility of the wrap disclosed and claimed herein is not limited to uses involving contact with human skin.

EXPERIMENTAL

Protocols

Tensile Strengths, % Elongation

Thwing-Albert

Tensile strength determines the maximum tension that a given sample can withstand without tearing (samples are described below in Examples 1–5). The tensile strength measurements allow comparison of the different perforation/separation lengths and their relative strength when stretched. Testing is conducted upon a THWING-ALBERT INTELECT™ II (Model No. 1450-42-C) constant rate of extension tensile tester equipped with clamp-type jaws manufactured by the Thwing-Albert Instrument Company of Philadelphia, Pa.

Rectangular test samples of 2.54 cm×22.86 cm (1"×9") are cut from a roll of the wrap to be tested. The long dimension is cut in the direction (machine or cross-machine) to be tested. The ends of the test samples are folded adhesive-to-adhesive to form a two inch nonadhesive tab at each end. The nonadhesive tabs prevent the sample from being pulled out of the jaws, reducing premature jaw breaks and preventing the sample from leaving an adhesive residue on the jaws. The samples are positioned within the jaws of the Thwing-Albert tester and the tester set at a crosshead speed of 5 inches per minute, a chart speed of 10 inches per minute and a gauge length of 5 inches. The chart recorder is set at 0.1 inch per chart division in the cross direction and 0.2 inch per chart division in the machine direction. The machine is activated and the sample pulled apart until the force required to pull the sample decreases.

Tensile strength is calculated in accordance with the equation set forth below where "Pen Height$_{max}$" is the number of small divisions in the cross direction reached by the pen in its maximum travel across the chart.

$$\text{Tensile Strength} = (\text{Load Range})(\text{Pen Height}_{max})/(100)$$

Samples having high tensile strengths are desirable since high tensile strength indicates that the sample can withstand a large tension without breaking.

Elongation is calculated in accordance with the equation set forth below where "Pen Distance$_{max}$" is the number of small divisions reached by the pen in the machine direction from initiation of pen deflection to sample break.

$$\% \text{ Elongation} = \frac{(20)(\text{Pen Distance}_{max})(\text{Crosshead Speed})}{(\text{Gauge Length})(\text{Chart Speed})}$$

The higher the percent elongation for a given sample, the further the sample can be stretched without breaking. It is desirable that elastic wraps are stretchy, therefore, a high percent elongation is desirable.

Hand Tear Test

Opposite ends of the samples for Examples 1–5 were grasped between the thumb and forefinger of each hand and then rapidly pulled in a pull apart motion with one hand pulling toward the body and one hand pulling away from the body.

The resulting tear for each sample was evaluated according to the following scale:

| | |
|---|---|
| 0 | no tear |
| 1 | poor |
| 2 | fair |
| 3 | acceptabele |
| 4 | good |
| 5 | excellent |

The higher the result on the hand tear test, the more desirable the sample or the easier the sample is to tear. Results from the Hand Tear Test are set forth in Tables 2 through 6 below.

% Machine Direction Tensile Strength of Perforated vs. Nonperforated Samples For each of the samples of Examples 1–5 below, the machine direction tensile strength was tested for a nonperforated sample as well as for a perforated sample. The tensile strength of the perforated samples as compared to the nonperforated sample is shown as a percentage in the last column of Tables 2–6 below. A perforated sample having 100% of the tensile strength of its nonperforated counterpart is ideal.

Test Samples

Perforating

Samples for Examples 1–5 were perforated as follows. Samples were made in increments of about 15 cm wide by about 10 m long. The wraps were then laterally perforated with a rotary die to form separation lines with linear perforations. The perforation lines were about 5.08 cm (2 inches) apart. The perforations had perforation lengths, connecting segment lengths and a ratio of perforation to connecting segment lengths as specified in Tables 2–6. Test samples were prepared using a 2.54 cm by 10 cm rule die oriented lengthwise along the machine direction of the wrap. Three samples were taken across the width of the wrap by placing the die on the wrap and striking it sharply to cut each test sample for evaluation. The perforated wraps were then tested for Tearability (Hand Tear Test) Average Machine Direction Tensile Strength ($T_{MD}$) and Average Machine Direction Elongation ($E_{MD}$). The nonperforated counterpart of each sample was also tested for Average Machine Direction Elongation to allow the comparison for Percent Machine Direction Tensile for Perforated vs. Nonperforated Sample. The results for each test are set forth in Tables 2 through 6 below.

EXAMPLE 1

A 10 m long and 150 mm wide piece of Coban™ 1584 self-adherent wrap (available from Minnesota Mining and Manufacturing Company, St. Paul, Minn.) was perforated as described above. The wrap consisted of two layers of nonwoven web with one layer of spandex filaments bonded between the layers using a natural rubber latex binder as described in U.S. Pat. Nos. 3,575,782 and 4,984,584 herein incorporated by reference.

Evaluations of these perforated samples are set forth in Table 2. Sample numbers 7, 8, 9 and 10 were acceptable and sample number 11 was preferred.

EXAMPLE 2

A 10 m length of 150 mm wide nonwoven meltblown polyurethane web coated with an acrylate adhesive was dispensed on a release liner and was perforated as described above.

The web is commercially available in a converted (cut and shaped) form as SteriStrips™ brand wound closure strips (3M Co., St. Paul, Minn.). The melt blown web basis weight was 85–90 g/m² and the web was about 0.30–0.33 mm thick. The web and processes for its preparation are described in U.S. Pat. No. 5,230,701 herein incorporated by reference.

Evaluations of these perforated webs are set forth below in Table 3. Samples 9 and 10 were acceptable whereas sample Number 7 was preferred.

EXAMPLE 3

A 10 m length of 150 mm wide chemically blown polyvinylchloride foam having a thickness of 0.889 mm and coated with an acrylic pressure sensitive adhesive was tested. The foam tape is available as Microfoam™ Surgical Tape (3M Company, St. Paul, Minn.).

The foam was perforated as described above. Table Four sets forth the results of evaluating the perforated samples. Sample numbers 7 and 11 were acceptable and sample number 13 was preferred.

EXAMPLE 4

A 10 m length of 150 mm wide hydroentangled polyester nonwoven fabric (HEF 140-084 available from Veratec, Inc., Walpole, Mass.) which had been creped on a Micrex® machine (available from Bird Machine Co., Walpole, Mass.) was impregnated with about 16% by weight of elastomeric binder (Hystretch V-43 available from B. F. Goodrich Co., Akron, Ohio) and then coated with an acrylate pressure sensitive adhesive (97:3 isooctyl acrylate:acrylamide). The process of manufacture used is described in U.S. Pat. No. 4,366,814 and is herein incorporated by reference.

The samples were perforated and evaluated as described above. Evaluation results are set forth in Table 7. Sample 7 was acceptable and Sample 9 was preferred.

EXAMPLE 5

A 10 m length of 150 mm wide hydroentangled polyester nonwoven fabric having a thickness of about 0.55–0.58 mm which was chemically bonded with an elastomeric binder (SF 9309.1 available from Veratec, Inc. Walpole, Mass.) and coated on one side with the acrylic pressure sensitive adhesive used on the samples in Example D was perforated as described above. The manufacturing process used is described in U.S. Pat. No. 4,366,814 which is herein incorporated by reference.

The samples were perforated and evaluated as described above and results are set forth in Table 6. Sample 10 was acceptable and Sample 5 was preferred.

TABLE TWO

| | Separation Lines | | | Perforated Tape Test Results | | | |
|---|---|---|---|---|---|---|---|
| Example A Sample # | Perforation Length in mm | Connecting Segment Length in mm | Cut to Uncut Ratio | Hand Tear Test | Tensile; $T_{MD}$ (in g/cm) | % Elongation; $E_{MD}$ | %$_{MD}$Tensile; Perforated vs. Non-perforated |
| 1 | 3.18 | 0.41 | 7.75:1 | 5 | 548 | 150 | 26.0 |
| 2 | 3.18 | 0.51 | 6.24:1 | 5 | 572 | 150 | 27.1 |
| 3 | 1.98 | 0.41 | 4.83:1 | 5 | 720 | 150 | 34.1 |
| 4 | 1.98 | 0.51 | 3.88:1 | 4 | 978 | 190 | 46.4 |
| 5 | 1.56 | 0.25 | 6.24:1 | 5 | 697 | 150 | 33.0 |
| 6 | 1.56 | 0.41 | 3.80:1 | 4 | 972 | 185 | 46.0 |
| 7 | 1.56 | 0.51 | 3.06:1 | 4 | 1112 | 190 | 52.7 |
| 8 | 1.19 | 0.25 | 4.76:1 | 5 | 1029 | 195 | 48.8 |
| 9 | 1.19 | 0.41 | 2.90:1 | 4 | 1117 | 200 | 52.9 |
| 10 | 1.05 | 0.25 | 4.20:1 | 4 | 1199 | 205 | 56.8 |
| 11 | 1.19 | 0.51 | 2.33:1 | 4 | 1323 | 220 | 62.7 |
| 12 | 0.79 | 0.25 | 3.16:1 | 3 | 1310 | 200 | 62.1 |
| 13 | 0.79 | 0.41 | 1.93:1 | 1 | 1940* | 225 | 91.9 |
| Control | — | — | — | 1 | 2110 | 230 | — |

*Did not tear along perforation

TABLE THREE

| Example B Sample # | Separation Lines | | | Perforated Tape Test Results | | | |
|---|---|---|---|---|---|---|---|
| | Perforation Length in mm | Connecting Segment Length in mm | Cut to Uncut Ratio | Hand Tear Test | Tensile; $T_{MD}$ (in g/cm) | % Elongation; $E_{MD}$ | %$_{MD}$Tensile; Perforated vs. Non-perforated |
| 1 | 3.18 | 0.41 | 7.75:1 | 5 | 268 | 33 | 21.4 |
| 2 | 3.18 | 0.51 | 6.24:1 | 5 | 332 | 46 | 26.5 |
| 3 | 1.98 | 0.41 | 4.83:1 | 5 | 372 | 67 | 29.8 |
| 4 | 1.98 | 0.51 | 3.88:1 | 5 | 443 | 99 | 35.4 |
| 5 | 1.56 | 0.25 | 6.24:1 | 5 | 331 | 51 | 26.5 |
| 6 | 1.56 | 0.41 | 3.80:1 | 5 | 443 | 97 | 35.4 |
| 7 | 1.56 | 0.51 | 3.06:1 | 5 | 588 | 180 | 47.0 |
| 8 | 1.19 | 0.25 | 4.76:1 | 5 | 452 | 107 | 36.2 |
| 9 | 1.19 | 0.41 | 2.90:1 | 4 | 661 | 190 | 52.9 |
| 10 | 1.05 | 0.25 | 4.20:1 | 4 | 506 | 131 | 40.5 |
| 11 | 1.19 | 0.51 | 2.33:1 | 4 | 779 | 223 | 62.3 |
| 12 | 0.79 | 0.25 | 3.16:1 | 3 | 661 | 186 | 52.9 |
| 13 | 0.79 | 0.41 | 1.93:1 | 2 | 946 | 276 | 76.5 |
| Control | — | — | — | 0 | 1250 | 350 | — |

TABLE FOUR

| Example C Sample # | Separation Lines | | | Perforated Tape Test Results | | | |
|---|---|---|---|---|---|---|---|
| | Perforation Length in mm | Connecting Segment Length in mm | Cut to Uncut Ratio | Hand Tear Test | Tensile; $T_{MD}$ (in g/cm) | % Elongation; $E_{MD}$ | %$_{MD}$Tensile; Perforated vs. Non-perforated |
| 1 | 3.18 | 0.41 | 7.75:1 | 5 | 268 | 32 | 24 |
| 2 | 3.18 | 0.51 | 6.24:1 | 3 | 620 | 76 | 56 |
| 3 | 1.98 | 0.41 | 4.83:1 | 4 | 427 | 49 | 39 |
| 4 | 1.98 | 0.51 | 3.88:1 | 5 | 590 | 79 | 53 |
| 5 | 1.56 | 0.25 | 6.24:1 | 3 | 414 | 48 | 37 |
| 6 | 1.56 | 0.41 | 3.80:1 | 5 | 479 | 58 | 43 |
| 7 | 1.56 | 0.51 | 3.06:1 | 5 | 599 | 81 | 54 |
| 8 | 1.19 | 0.25 | 4.76:1 | 5 | 438 | 47 | 40 |
| 9 | 1.19 | 0.41 | 2.90:1 | 3 | 779 | 105 | 70 |
| 10 | 1.05 | 0.25 | 4.20:1 | 5 | 568 | 67.0 | 51 |
| 11 | 1.19 | 0.51 | 2.33:1 | 5 | 600 | 68.0 | 54 |
| 12 | 0.79 | 0.25 | 3.16:1 | 4 | 554 | 60.0 | 50 |
| 13 | 0.79 | 0.41 | 1.93:1 | 5 | 686 | 87.5 | 62 |
| Control | — | — | — | 2 | 1106 | 200.0 | — |

TABLE FIVE

| Example D Sample # | Separation Lines | | | Perforated Tape Test Results | | | |
|---|---|---|---|---|---|---|---|
| | Perforation Length in mm | Connecting Segment Length in mm | Cut to Uncut Ratio | Hand Tear Test | Tensile; $T_{MD}$ (in g/cm) | % Elongation; $E_{MD}$ | %$_{MD}$Tensile; Perforated vs. Non-perforated |
| | 3.18 | 0.41 | 7.75:1 | 4 | 1180 | 35 | 20.7 |
| 2 | 3.18 | 0.51 | 6.21:1 | 3 | 1537 | 40 | 27.0 |
| 3 | 1.98 | 0.41 | 4.83:1 | 3 | 1752 | 42 | 30.7 |
| 4 | 1.98 | 0.51 | 3.88:1 | 3 | 2073 | 42 | 36.4 |
| 5 | 1.56 | 0.25 | 6.24:1 | 4 | 1430 | 35 | 25.1 |
| 6 | 1.56 | 0.41 | 3.80:1 | 3 | 2200 | 45 | 38.6 |
| 7 | 1.56 | 0.51 | 3.06:1 | 3 | 2753 | 53 | 48.3 |
| 8 | 1.19 | 0.25 | 4.76:1 | 4 | 1698 | 40 | 27.8 |
| 9 | 1.19 | 0.41 | 2.90:1 | 3 | 2931 | 53 | 51.4 |
| 10 | 1.05 | 0.25 | 4.20:1 | 3 | 2110 | 45 | 37.0 |
| 11 | 1.19 | 0.51 | 2.33:1 | 3 | 3242 | 57 | 58.6 |
| 12 | 0.79 | 0.25 | 3.16:1 | 2 | 3307 | 57 | 58.0 |
| 13 | 0.79 | 0.41 | 1.93:1 | 2 | 3682 | 65 | 64.6 |
| Control | — | — | — | 0 | 5700 | 92 | — |

TABLE SIX

| Example E Sample # | Separation Lines | | | Perforated Tape Test Results | | | |
|---|---|---|---|---|---|---|---|
| | Perforation Length in mm | Connecting Segment Length in mm | Cut to Uncut Ratio | Hand Tear Test | Tensile; $T_{MD}$ | % Elongation $E_{MD}$ (in g/cm) | %$_{MD}$Tensile; Perforated vs. Non-perforated |
| 1 | 3.18 | 0.41 | 7.75:1 | 5 | 661 | 7 | 21.8 |
| 2 | 3.18 | 0.51 | 6.21:1 | 5 | 930 | 9 | 30.6 |
| 3 | 1.98 | 0.41 | 4.83:1 | 5 | 1037 | 10 | 34.1 |
| 4 | 1.98 | 0.51 | 3.88:1 | 5 | 1233 | 12 | 40.6 |
| 5 | 1.56 | 0.25 | 6.24:1 | 5 | 1430 | 35 | 47.0 |
| 6 | 1.56 | 0.41 | 3.80:1 | 5 | 1162 | 10 | 38.2 |
| 7 | 1.56 | 0.51 | 3.06:1 | 4 | 1358 | 13 | 44.7 |
| 8 | 1.19 | 0.25 | 4.76:1 | 5 | 1020 | 9 | 33.5 |
| 9 | 1.19 | 0.41 | 2.90:1 | 4 | 1809 | 15 | 59.5 |
| 10 | 1.05 | 0.25 | 4.20:1 | 4 | 2377 | 24 | 78.2 |
| 11 | 1.19 | 0.51 | 2.33:1 | 3 | 2020 | 19 | 66.4 |
| 12 | 0.79 | 0.25 | 3.16:1 | 2 | 2735 | 25 | 89.9 |
| 13 | 0.79 | 0.41 | 1.93:1 | 2 | 2002 | 18 | 65.9 |
| Control | — | — | — | 0 | 3040 | 37 | — |

The Examples and the data in the corresponding Tables 2–6 illustrate that the present invention is both hand tearable and functional as an elastic wrap. That is, the invention wraps display the necessary tensile strength while still allowing hand tearing of the wraps. The most preferred wraps demonstrate easy hand tearing (a large number resulting from the Hand Tear Test) and a high tensile strength (large numbers resulting from the Machine Direction Tensile Strength and Elongation).

We claim:

1. Elastic wrap comprising an elastic substrate which can be longitudinally elongated between about 7 to 280 percent, the substrate having a longitudinal axis and a lateral axis having a plurality of longitudinally spaced, laterally extending, perforated separation lines defined by a series of about 0.2 to 5 mm perforations separated by about 0.1 to 1 mm connecting segments of wrap and a ratio of perforation length to connecting segment length of about 1:1 to 10:1, said elastic substrate selected from the group consisting of foam, woven fabric and nonwoven web, wherein the perforated wrap exhibits longitudinal stretch and recovery across said perforations.

2. The wrap of claim 1 wherein the elastic substrate comprises a nonwoven web.

3. The wrap of claim 1 wherein the nonwoven web is coated on a major surface with a pressure sensitive adhesive.

4. The wrap of claim 3 further comprising a low adhesion backsize coated on a major surface of the elastic substrate.

5. The wrap of claim 2 wherein the nonwoven web further comprises elastic filaments bound to the nonwoven web with an elastomeric binder.

6. The wrap of claim 2 wherein the nonwoven web is hydroentangled and is impregnated with an elastomeric binder.

7. The wrap of claim 2 wherein the nonwoven web is comprised of polyester fibers.

8. The wrap of claim 1 wherein the elastic substrate comprises a foam.

9. The wrap of claim 8 wherein the foam comprises polyvinylchloride foam.

10. The wrap of claim 1 wherein the perforated separation lines are uniformly longitudinally spaced about 1 to 20 cm apart to define individually separable sheets of wrap having identical longitudinal lengths.

11. The wrap of claim 1 wherein the perforated separation lines are uniformly longitudinally spaced about 2 to 10 cm apart to define individually separable sheets of wrap having identical longitudinal lengths.

12. The wrap of claim 1 wherein the perforated separation lines are defined by perforations which are about 0.5 to 3 mm long, connecting segments which are about 0.2 to 0.8 mm long, and a ratio of perforation length to connecting segment length of about 1:1 to 6:1.

13. The wrap of claim 1 wherein the perforated separation lines are defined by perforations which are about 1 to 2 mm long, connecting segments which are about 0.2 to 0.6 mm long, and a ratio of perforation length to connecting segment length of about 1:1 to 3:1.

14. The wrap of claim 1 wherein the perforations are linear perforations which extend laterally across the wrap.

15. The wrap of claim 1 wherein the perforations are linear perforations which extend at an angle of about 30° to 60° from the lateral axis of the wrap.

16. The wrap of claim 1 wherein the perforations are nonlinear perforations.

17. The wrap of claim 1 wherein the perforations in each separation line have a uniform length.

18. The wrap of claim 13 wherein the perforations in each separation line have a uniform shape.

19. The wrap of claim 1 wherein the wrap can be longitudinally elongated between about 150 to 230 percent.

20. A roll of elastic wrap comprising:
   a. a core, and
   b. a length of elastic wrap wound around the core;
   c. wherein the wrap comprises at least (i) an elastomeric binder-containing nonwoven fabric, and (ii) a plurality of longitudinally spaced, laterally extending, perforated separation lines defined by a plurality of about 0.2 to 5 mm perforations separated by about 0.1 to 1 mm connecting segments of tape and a ratio of perforation length to connecting segment length of about 1:1 to 10:1, wherein the perforated wrap exhibits longitudinal stretch and recovery across said perforations.

21. A method of dispensing elastic wrap comprising the steps of:
   a. unwinding a length of wrap from a roll of the wrap wherein the wrap comprises a binder-containing nonwoven web which includes a plurality of longitudinally spaced, laterally extending, perforated separation lines defined by a plurality of about 0.2 to 5 mm perforations separated by about 0.1 to 1 mm connecting segments of wrap and a ratio of perforation length to connecting segment length of about 1:1 to 10:1 wherein the perforated wrap exhibits longitudinal stretch and recovery across said perforations, and b. laterally tearing the wrap along a separation line to detach a length of wrap from the tape remaining on the core.

22. A roll of elastic wrap comprising an elastomeric binder-containing nonwoven web having a longitudinal axis and a lateral axis which is coated on a major surface with a cohesive material; the cohesively-coated web having a plurality of longitudinally spaced, laterally extending, perforated separation lines defined by a series of about 0.2 to 5 mm perforations separated by about 0.1 to 1 mm connecting segments of dressing and a ratio of perforation length to connecting segment length of about 1:1 to 10:1 wherein the perforated wrap exhibits longitudinal stretch and recovery across said perforations.

23. Elastic wrap comprising an elastic substrate which can be longitudinally elongated between about 25 to 280 percent, the substrate having a longitudinal axis and a lateral axis having a plurality of longitudinally spaced, laterally extending, perforated separation lines defined by a series of about 0.2 to 5 mm perforations separated by about 0.1 to 1 mm connecting segments of wrap and a ratio of perforation length to connecting segment length of about 1:1 to 10:1 wherein the perforated wrap exhibits longitudinal stretch and recovery across said perforations.

* * * * *

UNITED STATES PATENT AND TRADEMARK OFFICE
CERTIFICATE OF CORRECTION

PATENT NO.: 5,616,387
DATED: 1 April 1997
INVENTOR(S): Augst et al.

It is certified that error appears in the above-identified patent and that said Letters Patent is hereby corrected as shown below:

Col. 1, line 5, delete "Continuation" and insert --continuation--.

Col. 16, line 48, before "a" insert --a.--.

Col. 16, line 56, delete "tape" and insert --wrap--.

Col. 16, line 63, before "wherein" insert --comprising a core and a length of elastic wrap around the core;--.

Col. 17, line 6, delete "tape" and insert --wrap--.

Col. 17, line 15, delete "dressing" and insert --wrap--.

Signed and Sealed this

Eighteenth Day of August, 1998

Attest:

BRUCE LEHMAN

Attesting Officer

Commissioner of Patents and Trademarks